US009357956B2

(12) United States Patent
Uematsu et al.

(10) Patent No.: US 9,357,956 B2
(45) Date of Patent: Jun. 7, 2016

(54) SPECTROSCOPIC SENSOR AND ELECTRONIC APPARATUS

(75) Inventors: Akira Uematsu, Suwa (JP); Noriyuki Nakamura, Sakata (JP); Akira Komatsu, Kamiina-gun (JP); Kunihiko Yano, Shiogiri (JP)

(73) Assignee: SEIKO EPSON CORPORATION, Tokyo (JP)

(*) Notice: Subject to any disclaimer, the term of this patent is extended or adjusted under 35 U.S.C. 154(b) by 439 days.

(21) Appl. No.: 13/038,992

(22) Filed: Mar. 2, 2011

(65) Prior Publication Data

US 2011/0215432 A1 Sep. 8, 2011

(30) Foreign Application Priority Data

Mar. 5, 2010 (JP) ................................ 2010-048850

(51) Int. Cl.
*H01L 31/0232* (2014.01)
*A61B 5/1455* (2006.01)
*H01L 31/0216* (2014.01)
*H01L 31/103* (2006.01)

(52) U.S. Cl.
CPC ...... *A61B 5/14552* (2013.01); *H01L 31/02162* (2013.01); *H01L 31/02325* (2013.01); *H01L 31/103* (2013.01)

(58) Field of Classification Search
USPC ............................ 257/432, 434, 439, E31.127
See application file for complete search history.

(56) References Cited

U.S. PATENT DOCUMENTS

| 7,623,166 | B2 | 11/2009 | Inaba et al. | |
|---|---|---|---|---|
| 2005/0133879 | A1* | 6/2005 | Yamaguti et al. | 257/435 |
| 2006/0275944 | A1* | 12/2006 | Hyun | 438/70 |
| 2006/0285005 | A1* | 12/2006 | Inaba et al. | 348/340 |

FOREIGN PATENT DOCUMENTS

| JP | A-6-129908 | 5/1994 |
|---|---|---|
| JP | A-2006-351800 | 12/2006 |
| JP | 2007-139591 A | 6/2007 |
| JP | 2009-182223 A | 8/2009 |

\* cited by examiner

*Primary Examiner* — Lynne Gurley
*Assistant Examiner* — Vernon P Webb
(74) *Attorney, Agent, or Firm* — Oliff PLC

(57) ABSTRACT

A spectroscopic sensor has plural angle limiting filters that limit incident angles of incident lights, plural light band-pass filters that transmit specific wavelengths, and plural photodiodes to which corresponding transmitted lights are input. The spectroscopic sensor is a semiconductor device in which the angle limiting filters, the light band-pass filters, and the photodiodes are integrated, and, assuming that the surface on which impurity regions for the photodiodes are formed is a front surface of a semiconductor substrate, holes for receiving lights are formed in the impurity regions from the rear surface side.

21 Claims, 17 Drawing Sheets

FRONT

REAR

SPECTROSCOPIC SENSOR AND ELECTRONIC APPARATUS

The entire disclosure of Japanese Patent Application No. 2010-048850, filed Mar. 5, 2010 is expressly incorporated by reference herein.

BACKGROUND

1. Technical Field

The present invention relates to a spectroscopic sensor, an electronic apparatus, etc.

2. Related Art

In medical, agricultural, environmental fields etc., spectroscopic sensors are used for diagnoses and inspections of objects. For example, in medical fields, pulse oximeters that measure oxygen saturation in the blood using light absorption of hemoglobin are used. Further, in the agricultural fields, sugar content meters that measure the sugar contents of fruits using light absorption of sugar.

However, in spectroscopic sensors in related art, there is a problem that downsizing is difficult. For example, in a spectroscopic sensor that acquires a continuous spectrum, it is necessary to provide a prism for generation of the continuous spectrum or the like and secure an optical path length, and the device becomes larger. Accordingly, it is difficult to provide many sensors, constantly provide sensors for an object to be inspected, or the like.

Here, Patent Document 1 (JP-A-6-129908) discloses a technique of limiting a transmission wavelength band of a filter by limiting the incident angle of incident light using an optical fiber. Further, Patent Document 2 (JP-A-2006-351800) discloses a technique of sensing light in plural wavelength bands using multilayer filters having different thicknesses with respect to each sensor.

SUMMARY

According to some aspects of the invention, a spectroscopic sensor, an electronic apparatus, etc. that can be downsized may be provided.

One aspect of the invention relates to a spectroscopic sensor including an impurity region for a photodiode formed on a semiconductor substrate, an angle limiting filter for limiting an incident angle of an incident light to a light receiving surface of the photodiode, and a light band-pass filter that transmits a specific wavelength of the incident light, wherein, assuming that the surface on which the impurity region for the photodiode is formed is a front surface of the semiconductor substrate, the angle limiting filter is formed using the semiconductor substrate left after formation of holes for receiving light in the impurity region for the photodiode from a rear surface side of the semiconductor substrate.

According to the one aspect of the invention, the angle limiting filter is formed using the semiconductor substrate left after formation of the holes for receiving light in the impurity region for the photodiode from the rear surface side of the semiconductor substrate, and the incident angle of the incident light to the light receiving area of the photodiode is limited by the angle limiting filter. Thereby, downsizing of the spectroscopic sensor or the like may be realized.

Further, in the one aspect of the invention, the light band-pass filter may have a transmission wavelength that varies in response to the incident angle of the incident light to the light receiving surface of the photodiode, the angle limiting filter may limit the incident angle of the incident light and limit a change range of the transmission wavelength, and, for the light band-pass filter, a band of the specific wavelength to be transmitted may be set according to the change range of the transmission wavelength limited by the angle limiting filter.

In this case, the band of the specific wavelength to be transmitted by the light band-pass filter may be set according to the incident angle limited by the angle limiting filter.

Furthermore, in the one aspect of the invention, the angle limiting filter may be formed along an outer circumference of a light receiving area of the photodiode in a plan view with respect to the semiconductor substrate.

In this case, in the plan view with respect to the semiconductor substrate, by forming the angle limiting filter along the outer circumference of the light receiving area of the photodiode, the incident angle of the incident light to the light receiving area of the photodiode may be limited.

In addition, in the one aspect of the invention, the angle limiting filter may have plural openings formed on the rear surface side of the semiconductor substrate, and the plural openings may be formed along an outer circumference of the light receiving area of the photodiode and may limit the incident angle of the incident light to the light receiving area of the photodiode.

In this case, the angle limiting filter has plural openings formed along the outer circumference of the light receiving area of the photodiode, and thereby, the incident angle of the incident light to the light receiving area of the photodiode may be limited.

Further, in the one aspect of the invention, the light band-pass filter may be formed by a multilayer thin film tilted at an angle in response to the transmission wavelength relative to the semiconductor substrate.

In this case, the light band-pass filter may be formed by the multilayer thin film tilted at the angle in response to the transmission wavelength relative to the semiconductor substrate.

Furthermore, in the one aspect of the invention, the light band-pass filter may be formed by plural sets of multilayer thin films having different transmission wavelengths, and the plural sets of multilayer thin films have different tilt angles relative to the semiconductor substrate in response to the transmission wavelengths and may be formed in a simultaneous thin film forming step.

In this case, the light band-pass filter may be formed by plural sets of multilayer thin films having different tilt angles relative to the semiconductor substrate in response to the transmission wavelengths and plural sets of multilayer thin films may be formed in the simultaneous thin film forming step.

In addition, in the one aspect of the invention, the impurity region for the photodiode may be sectioned into plural regions by an insulator having a trench structure, the light band-pass filter may be formed by plural band-pass filters having different transmission wavelengths, and each band-pass filter of the plural light band-pass filters may be provided in response to one or some regions sectioned by the insulator having the trench structure.

In this case, each band-pass filter of the plural light band-pass filters may be provided in response to one or some regions sectioned by the insulator having the trench structure.

Further, the one aspect of the invention may further include a tilted structure provided on the angle limiting filter, wherein the tilted structure may have a tilted surface tilted at an angle in response to the transmission wavelength of the light band-pass filter relative to the semiconductor substrate, and the multilayer thin film may be formed on the tilted surface.

In this manner, the multilayer thin film is formed on the tilted structure having the tilted surface tilted at the angle in response to the transmission wavelength of the light bandpass filter relative to the semiconductor substrate, and thereby, the multilayer thin film tilted at the angle in response to the transmission wavelength relative to the semiconductor substrate may be formed.

Furthermore, in the one aspect of the invention, the tilted structure may be formed on the angle limiting filter using a semiconductor process.

In this manner, the tilted structure may be formed on the angle limiting filter using the semiconductor process.

In addition, in the one aspect of the invention, the tilted structure may be formed by forming a step or a sparse and dense pattern on a transparent film stacked by the semiconductor process, and performing at least one of grinding and etching on the step or the sparse and dense pattern.

In this case, the tilted structure may be formed on the angle limiting filter using the semiconductor process by performing at least one of grinding and etching on the transparent film on which the step or the sparse and dense pattern has been formed.

Further, in the one aspect of the invention, a light blocking material may be provided on the rear surface of the semiconductor substrate left after formation of the holes for receiving light and wall surfaces of the holes for receiving light.

In this manner, the light blocking material may be provided on the rear surface of the semiconductor substrate left after formation of the holes for receiving light and the wall surfaces of the holes for receiving light.

Furthermore, in the one aspect of the invention, the light blocking material may be a light absorbing material or a light reflecting material.

In this case, the light blocking material may be formed using the light absorbing material or the light reflecting material.

In addition, another aspect of the invention relates to an electronic apparatus including the spectroscopic sensor according to the above aspect.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1A:
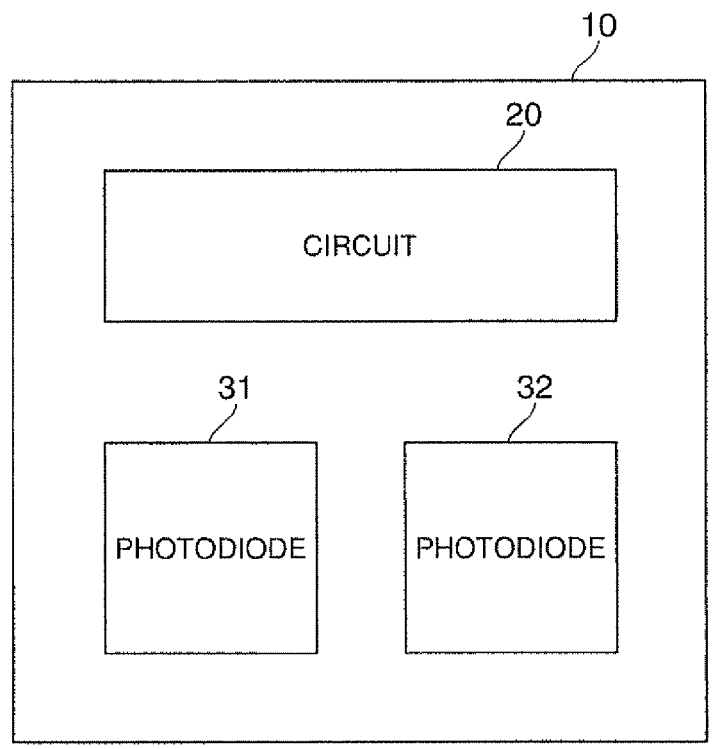
FIGS. 1A and 1B show a configuration example of a spectroscopic sensor of the embodiment.

Hereinafter, preferred embodiments of the invention will be described in detail. Note that the embodiments described as below do not unduly limit the subject matter of the invention described in claims, and all of the configurations explained in the embodiments are not necessarily essential as solving means of the invention.

1. Configuration Example

As described above, in medical, health fields or the like, small spectroscopic sensors that are constantly wearable are required, and there is a task of requiring downsizing of the spectroscopic sensors. For example, when the wavelength to be measured is known, a sensor that does not acquire its continuous spectrum but measures only the known wavelength may be provided.

However, there is a task of improving wavelength selectivity of the spectroscopic sensor. For example, if an angle limiting filter and a multilayer filter that determine the transmission wavelength band are formed in members, the light is diffused and attenuated on the bonded surfaces of the members, and the wavelength selectivity becomes lower.

Further, for example, in the above described Patent Document 1, a technique of limiting the transmission wavelength band of a filter by limiting the incident angle of incident light using an optical fiber is disclosed. However, according to the technique, if the numerical aperture of the optical fiber is made smaller for narrowing the band, the transmittance of the incident light becomes lower and the wavelength selectivity becomes lower.

Furthermore, there is a task of simplifying the manufacturing process of the spectroscopic sensor. For example, in Patent Document 2, a technique using multilayer filters having different film thicknesses with respect to each sensor is disclosed. However, according to the technique, separate multilayer film forming steps are necessary with respect to each film thickness, and the forming steps of the multilayer films become complex.

Accordingly, in the embodiment, downsizing of the spectroscopic sensor is realized in a simple manufacturing process by forming the angle limiting filter using silicon trenches and by forming the multilayer filter using a semiconductor process.

A configuration example of the spectroscopic sensor of the embodiment will be explained using FIGS. 1A to 2. As below, the configuration of the spectroscopic sensor of the embodiment will be schematically shown for simplicity, and the dimensions and ratios in the drawings are different from those of the real one.

Figure 1B:
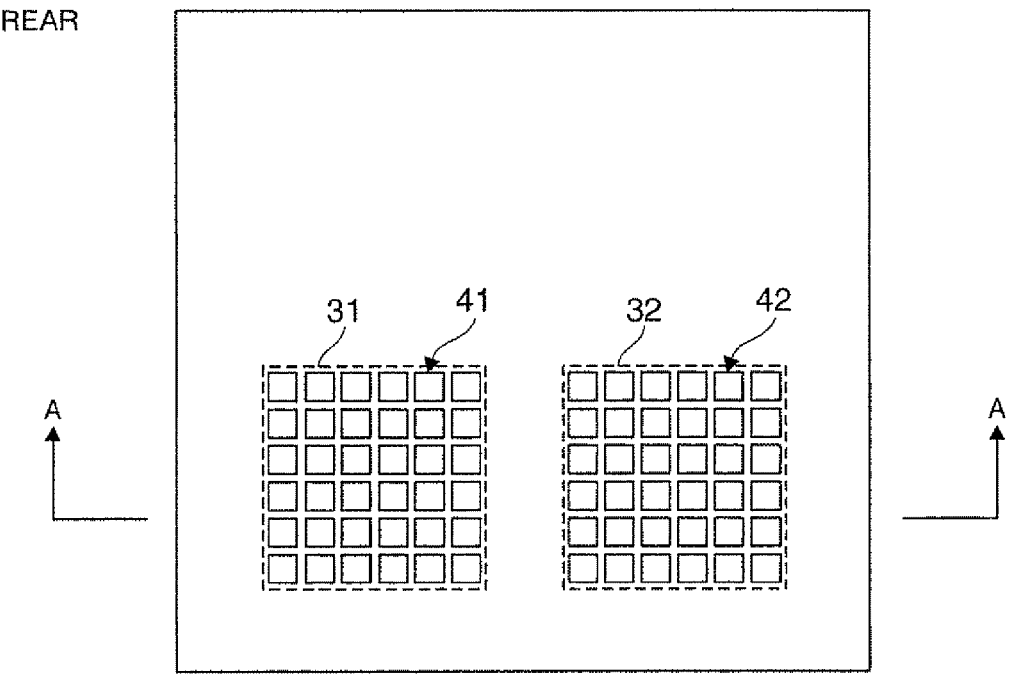

FIGS. 1A and 1B show plan views with respect to a semiconductor substrate 10 on which the spectroscopic sensor is formed. The spectroscopic sensor shown in FIGS. 1A and 1B includes the semiconductor substrate 10, a circuit 20, a first photodiode 31 (an impurity region for a first photosensor and the first photodiode in a broad sense), a second photodiode 32 (an impurity region for a second photosensor and the second photodiode in a broad sense), a first angle limiting filter 41, and a second angle limiting filter 42. As will be described later, multilayer filters are formed on the angle limiting filters 41, 42, however, their illustration will be omitted in FIGS. 1A and 1B.

FIG. 1A is the plan view seen from the front side on which impurity regions, wiring layers, etc. are formed in the plan view seen from a direction perpendicular to the plane of the semiconductor substrate 10. The semiconductor substrate 10 includes a P-type or N-type silicon substrate (silicon wafer), for example. On the front side of the semiconductor substrate 10, the photodiodes 31, 32 and the circuit 20 are formed using a semiconductor process. The circuit 20 includes amplifiers that process output signals from the photodiodes 31, 32, A/D conversion circuits, etc., for example.

FIG. 1B is the plan view seen from the rear side in the plan view seen from a direction perpendicular to the plane of the semiconductor substrate 10. On the rear side of the semiconductor substrate 10, the angle limiting filters 41, 42 are formed using silicon trenches toward the photodiodes 31, 32 formed on the front side. The angle limiting filters 41, 42 are formed in lattice forms in the plan view, for example, and limit the incident angles of incident lights entering the photodiodes 31, 32 from the rear side of the semiconductor substrate 10.

Here, the silicon trench is a technique of trenching the semiconductor substrate 10 using a semiconductor process or MEMS (Micro-Electro-Mechanical System). For example, it is a technique of forming holes, grooves, steps, or the like by dry etching on a silicon substrate.

Note that the configuration of the spectroscopic sensor of the embodiment is not limited to the configuration in FIGS. 1A, 1B, but various changes may be made by omitting part of its component elements (e.g., the circuit 20), or adding other component elements. For example, the numbers of photodiodes and angle limiting filters may be two as described above, or may be one or more. Further, the angle limiting filters 41, 42 may have lattice forms in the plan view as described above, or other forms.

Figure 2:
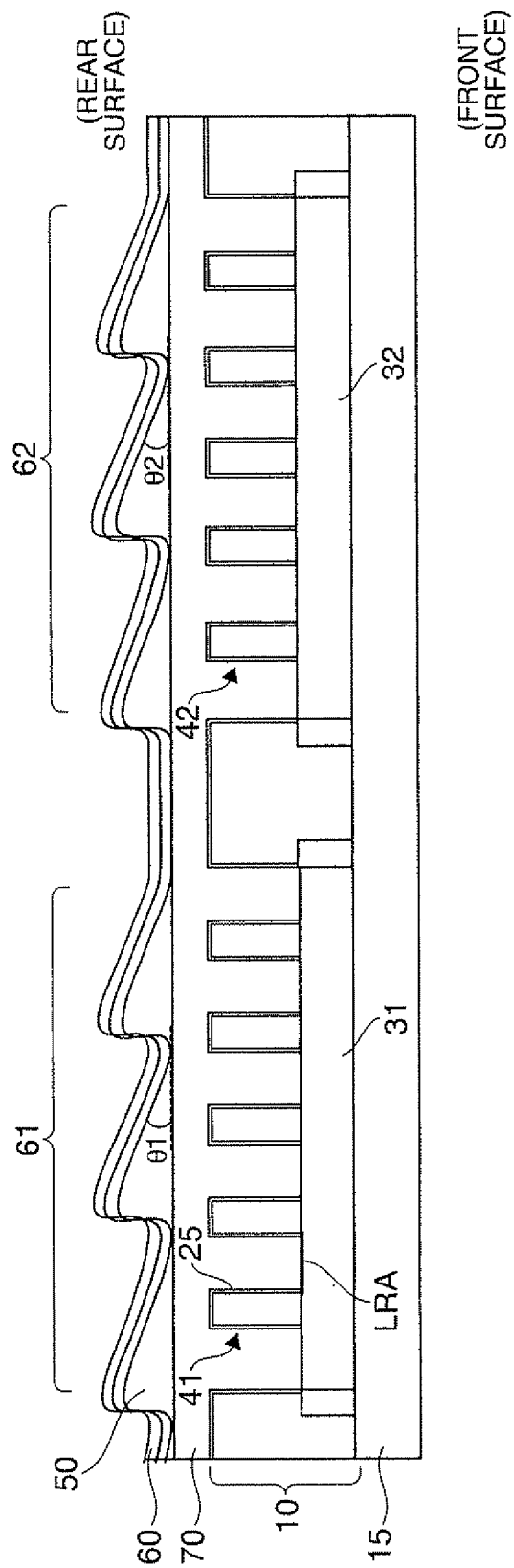
FIG. 2 shows a configuration example of the spectroscopic sensor of the embodiment.

FIG. 2 shows a sectional view of the spectroscopic sensor along A-A section shown in FIG. 1B. The spectroscopic sensor shown in FIG. 2 includes the semiconductor substrate 10, a wiring layer 15, light blocking materials 25, photodiodes 31, 32, the angle limiting filters 41, 42, the tilted structure 50 (angular structure), a first light band-pass filter 61 (a first multilayer filter, a first dielectric filter), and a second light band-pass filter 62 (a second multilayer filter, a second dielectric filter), and an insulating layer 70 (a transparent film in a broad sense).

Here, "on" in the embodiment refers to a direction perpendicular to the plane of the semiconductor substrate 10 and away from the semiconductor substrate 10.

As shown in FIG. 2, the photodiodes 31, 32 are formed on the front side of the semiconductor substrate 10. As will be described later, the photodiodes 31, 32 are formed by forming impurity regions using ion implantation or the like. For example, the photodiodes 31, 32 are realized by P-N junction between an N-type impurity region formed on a P-substrate and the P-substrate. Alternatively, they are realized by P-N junction between a P-type impurity region formed on a deep N-well (N-type impurity region) and the deep N-well.

On the photodiodes 31, 32, the wiring layer 15 is formed. The wiring layer 15 is stacked at forming steps of the above described circuit 20 etc., and formed by insulating layers of $SiO_2$ or the like, a wiring layer of aluminum wiring or the like, and contacts of tungsten plugs or the like. The output signals from the photodiodes 31, 32 are input to the above described circuit 20 etc. by the wirings within the wiring layer 15, and detection-processed.

On the rear side of the semiconductor substrate 10, the angle limiting filters 41, 42 are formed. The angle limiting filters 41, 42 are formed by the semiconductor substrate 10 left after silicon trenching. On side surfaces (wall surfaces) of holes trenched by silicon trenching and the rear side of the semiconductor substrate 10, the light blocking material 25 (light absorbing materials or light reflecting materials) are provided (formed, stacked). On the other hand, on the bottom surfaces of the holes as light receiving surfaces of the photodiodes, no light blocking material is provided. Further, the wall surfaces of the holes trenched by silicon trenching become wall surfaces of the angle limiting filters 41, 42, and block light so that incident lights at limited angles or more may not enter the photodiodes 31, 32. The aspect ratios of the lengths of the bottom sides (e.g., the longest diagonal lines of the bottom surfaces or the longer diameters) to the heights of the angle limiting filters 41, 42 are set in response to the transmission wavelength bands (e.g., BW1, BW2, which have been described later in FIG. 7B) of the light band-pass filters 61, 62.

On the angle limiting filters 41, 42, the insulating film 70 filling the opening parts (hollow parts) of the angle limiting filters 41, 42 is formed. For example, the insulating film 70 is formed by an insulating film of $SiO_2$ (silicon oxide film) or the like. Note that the insulating film 70 does not necessarily have an insulation property as long as it may be a transparent material with respect to the wavelengths detected by the photodiodes 31, 32.

On the insulating film 70, the tilted structure 50 is formed. The tilted structure 50 has tilted surfaces at different tilt angles in response to the transmission wavelengths of the light band-pass filters 61, 62. Specifically, as tilted surfaces for the incident light of the photodiode 31, plural tilted surfaces at a tilt angle θ1 relative to the plane of the semiconductor substrate 10 are formed, and, as tilted surfaces for the incident light of the photodiode 32, plural tilted surfaces at a tilt angle θ2 different from the tilt angle θ1 are formed. As will be described later, the tilted structure 50 is formed by processing the insulating films of $SiO_2$ or the like, for example, by etching, CMP (Chemical Mechanical Polishing), a gray scale lithography technology, or the like.

On the tilted structure 50, a multilayer thin film 60 forming the light band-pass filters 61, 62 is stacked. The transmission wavelength bands of the light band-pass filters 61, 62 are determined by the tilt angles θ1, θ2 of the tilted structure 50 and incident light limited angles (aspect ratios) of the angle limiting filters 41, 42. The light band-pass filters 61, 62 have configurations by which transmission wavelengths vary in response to the tilt angles, and not stacked at separate steps with respect to each transmission wavelength but stacked at the same multilayer film forming steps.

As described above, in the spectroscopic sensor in related art, there are tasks of improving wavelength selectivity of the spectroscopic sensor and simplifying the manufacturing process.

In this regard, according to the embodiment, the spectroscopic sensor includes the impurity regions for the photodiodes 31, 32 formed on the semiconductor substrate, the angle limiting filters 41, 42 for limiting the incident angles of incident lights to the light receiving areas of the photodiodes 31, 32, and the light band-pass filters 61, 62 that transmit specific wavelengths of the incident lights. Further, the angle limiting filters 41, 42 are formed by forming holes for receiving lights in which light blocking materials 25 (light absorbing films or light reflecting films) are provided on the wall surfaces and the rear side surfaces towards the impurity regions for the photodiodes 31, 32 from the rear side of the semiconductor substrate 10.

Thereby, the spectroscopic sensor may be formed using the semiconductor process or the MEMS technology, and downsizing of the spectroscopic sensor or the like may be realized. That is, the photodiodes 31, 32 are formed by the semiconductor process and the angle limiting filters 41, 42 are formed by rear side trenching of the semiconductor substrate 10, and thus, microfabrication may easily be performed and downsizing may be realized. Further, compared to the case where the angle limiting filters etc. are formed by separate members and the spectroscopic sensor is formed by bonding the separate members, the wavelength selectivity of transmission wavelengths may be improved. Furthermore, for example, compared to the case of using optical fibers as the angle limiting filters, reduction of transmitted lights due to the reduction of limited angles (numerical apertures) may be suppressed, and the wavelength selectivity may be improved.

Here, the light receiving areas of the photodiodes refer to areas on the impurity regions for the photodiodes 31, 32 into which incident lights that have passed through the angle limiting filters 41, 42 enter. For example, in FIG. 1B, they are areas corresponding to the respective openings of the lattice-formed angle limiting filters 41, 42. Alternatively, in FIG. 2, they are areas (for example, areas LRA) surrounded by the semiconductor substrate 10 (or the light blocking materials 25) forming the angle limiting filters 41, 42.

Further, the semiconductor process refers to a process of forming transistors, resistance elements, capacitors, insulating layers, wiring layers, etc. on a semiconductor substrate. For example, the semiconductor process includes an impurity introduction process, a thin film formation process, a photolithography process, an etching process, a planarization process, and a thermal treatment process.

Furthermore, in the embodiment, the angle limiting filters 41, 42 are formed along the outer circumferences of the light receiving areas of the photodiodes 31, 32 in the plan view with respect to the semiconductor substrate 10. Specifically, plural light receiving areas are set in the impurity regions for the photodiodes 31, 32, and plural openings are formed along the outer circumferences of the plural light receiving areas. For example, as shown in FIGS. 1A and 1B, square light blocking materials (light absorbing materials or light reflecting materials) surround the respective light receiving areas in the plan view, and the squares are arranged in the lattice forms to form the angle limiting filters 41, 42.

In this manner, the angle limiting filters 41, 42 are formed along the outer circumferences of the respective light receiving areas of the photodiodes 31, 32, and thus, the incident angles of the incident lights to the respective light receiving areas of the photodiodes 31, 32 may be limited.

Note that the embodiment is not limited to the case where the angle limiting filters 41, 42 have plural openings, however, the impurity regions for the photodiodes 31, 32 may be the respective one light receiving areas, and the respective one angle limiting filters to surround the outer circumferences of the impurity regions may be formed. Further, the embodiment is not limited to the case where the angle limiting filters 41, 42 are closed along the outer circumferences of the light receiving areas, but they may have discontinuous parts along the outer circumferences or be intermittently arranged along the outer circumferences.

Furthermore, in the embodiment, the light band-pass filters 61, 62 are formed using multilayer thin films tilted at the angles $\theta 1$, $\theta 2$ in response to the transmission wavelengths relative to the semiconductor substrate 10. More specifically, the light band-pass filters 61, 62 are formed using plural sets of multilayer thin films each set of which has different transmission wavelengths. Further, the plural sets of multilayer thin films have different tilt angles $\theta 1$, $\theta 2$ in response to the transmission wavelengths relative to the semiconductor substrate 10 and are formed at a simultaneous thin film forming step. For example, as shown in FIG. 2, one set of multilayer thin films are formed by continuously arranging the plural multilayer thin films at the tilt angle $\theta 1$. Alternatively, as will be described later in FIG. 5, multilayer thin films having different tilt angles $\theta 1$ to $\theta 3$ may be provided adjacent to each other, and, in the case where the multilayer thin films having the tilt angles $\theta 1$ to $\theta 3$ are repeatedly provided, one set of multilayer thin films may be formed by plural multilayer thin films having the same tilt angle $\theta 1$.

In this manner, the light band-pass filters 61, 62 may be formed using multilayer thin films tilted at the angles $\theta 1$, $\theta 2$ in response to the transmission wavelengths. Thereby, it is not necessary to stack the multilayer thin films having film thicknesses in response to the transmission wavelengths at separate step with respect to each transmission wavelength, and the forming step of the multilayer thin films may be simplified.

Here, the simultaneous thin film forming step refers not to a step of sequentially repeating the same step of forming a first set of multilayer thin films and then forming a second set of multilayer thin films, but to a step of forming plural sets of multilayer thin films at the same (simultaneous, single) thin film forming step.

Furthermore, in the embodiment, the spectroscopic sensor includes the tilted structure 50 provided on the angle limiting filters 41, 42. In addition, the tilted structure 50 has the tilted surfaces tilted at the angles $\theta 1$, $\theta 2$ in response to the transmission wavelengths of the light band-pass filters 61, 62 relative to the semiconductor substrate 10, and the multilayer thin films are formed on the tilted surfaces.

In this case, the multilayer thin films are formed on the tilted surfaces of the tilted structure 50, and the multilayer thin films tilted at the angles $\theta 1$, $\theta 2$ in response to the transmission wavelengths of the light band-pass filters 61, 62 may be formed.

Specifically, in the embodiment, the tilted structure 50 is formed on the angle limiting filters 41, 42 using the semiconductor process. For example, as will be described in FIG. 13 etc., the tilted structure 50 is formed by forming steps or a sparse and dense pattern on transparent films (insulating films) stacked using the semiconductor process, and performing at least one of grinding (e.g., CMP) and etching on the steps or the sparse and dense pattern.

In this manner, the tilted structure may be formed using the semiconductor process. Thereby, the forming step of the tilted structure may be simplified. Further, the cost may be reduced compared to the case where the tilted structure is formed using a separate member. Furthermore, the reduction of the amount of light on the bonded surface of the tilted structure as the separate member may be avoided.

Here, the steps of the insulating films are the level differences of the insulating film surfaces from the semiconductor substrate surface on the section of the semiconductor substrate. Further, the sparse and dense patterns of the insulating films are high and low patterns of the insulating film surfaces from the semiconductor substrate surface on the section of the semiconductor substrate, and the sparsity and density of the insulating films are formed according to the ratios of the higher parts and the lower parts.

Note that the tilted structure 50 may be formed not only by grinding or etching of the steps or the sparse and dense pattern, but using a gray scale lithography technology. In the gray scale lithography technology, the tilted structure is formed by exposing resists to light using a gray scale mask with dark and light parts, and performing etching using the exposed resists.

2. First Modified Example

In the embodiment, the configuration examples of forming the tilted structure 50 using the semiconductor process have been explained, and various modifications may be embodied in the embodiment.

Figure 3:
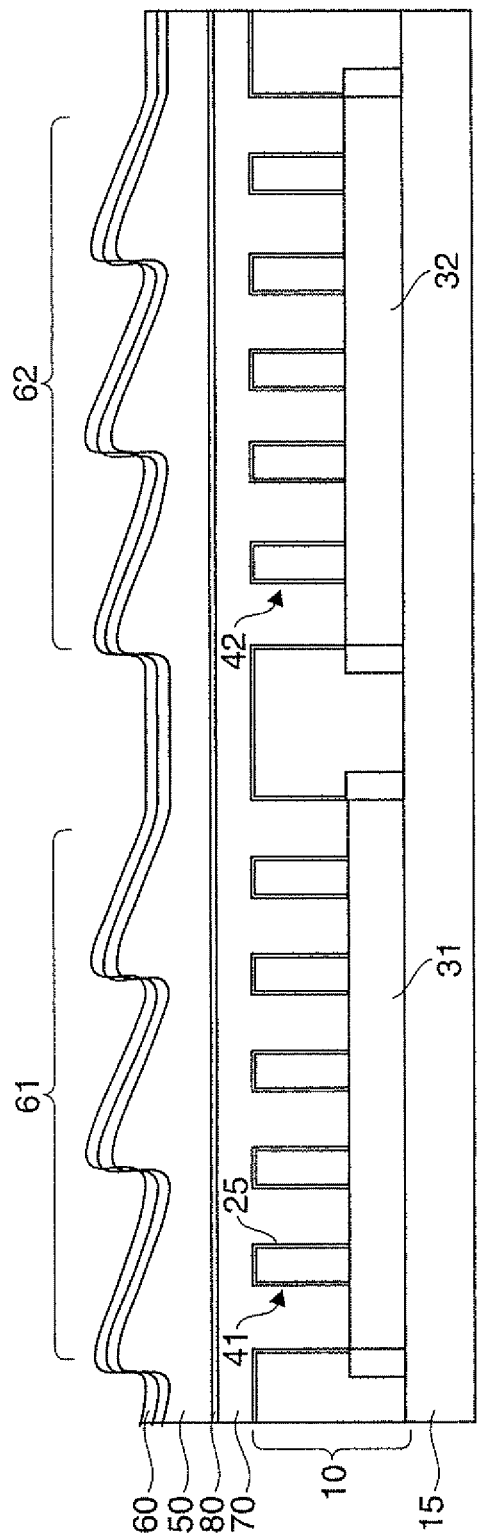
FIG. 3 shows a first modified example of the spectroscopic sensor.

FIG. 3 shows a first modified example of the spectroscopic sensor in which a tilted structure 50 is formed with a separate member and bonded. The spectroscopic sensor shown in FIG. 3 includes a semiconductor substrate 10, a wiring layer 15, light blocking materials 25, photodiodes 31, 32, angle limiting filters 41, 42, the tilted structure 50, light band-pass filters 61, 62, an insulating layer 70, and a bonding layer 80 (adhesive agent). As below, the same signs are assigned to the component elements described above in FIG. 2 etc., and their explanation will appropriately be omitted.

In the first modified example, the angle limiting filters 41, 42 and the insulating layer 70 are formed in the same manner as those of the above described configuration example. The tilted structure 50 is formed by a separate member of low-melting-point glass or the like, and tilted surfaces and multilayer thin films are formed on the tilted structure 50. Further, the tilted structure 50 and the insulating layer 70 are bonded using a transparent adhesive agent that transmits wavelengths to be sensed.

3. Second Modified Example

Figure 4:
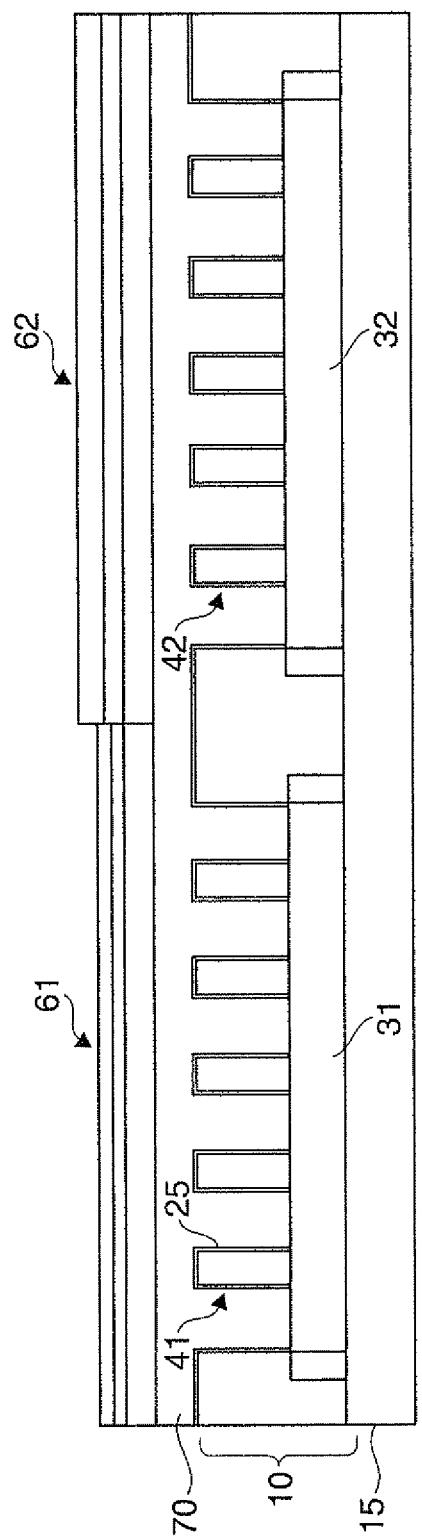
FIG. 4 shows a second modified example of the spectroscopic sensor.

FIG. 4 shows a second modified example of the spectroscopic sensor in which multilayer thin films in parallel to the semiconductor substrate 10 are formed without using the tilted structure 50. The spectroscopic sensor shown in FIG. 4 includes a semiconductor substrate 10, a wiring layer 15, light blocking materials 25, photodiodes 31, 32, angle limiting filters 41, 42, light band-pass filters 61, 62, and an insulating layer 70.

In the second modified example, the angle limiting filters 41, 42 and the insulating layer 70 are formed in the same manner as those of the above described configuration examples. Then, the multilayer thin films of the light band-pass filters 61, 62 are formed on the insulating layer 70. The multilayer thin films have different film thicknesses in response to the transmission wavelengths of the light band-pass filters 61, 62, and stacked at separate forming steps with respect to each transmission wavelength. That is, when one of the light band-pass filters 61, 62 is formed, the multilayer thin films are stacked while the other is covered by a photo resist or the like, and thereby, the multilayer thin films having different film thicknesses are formed.

4. Third Modified Example

Figure 5:
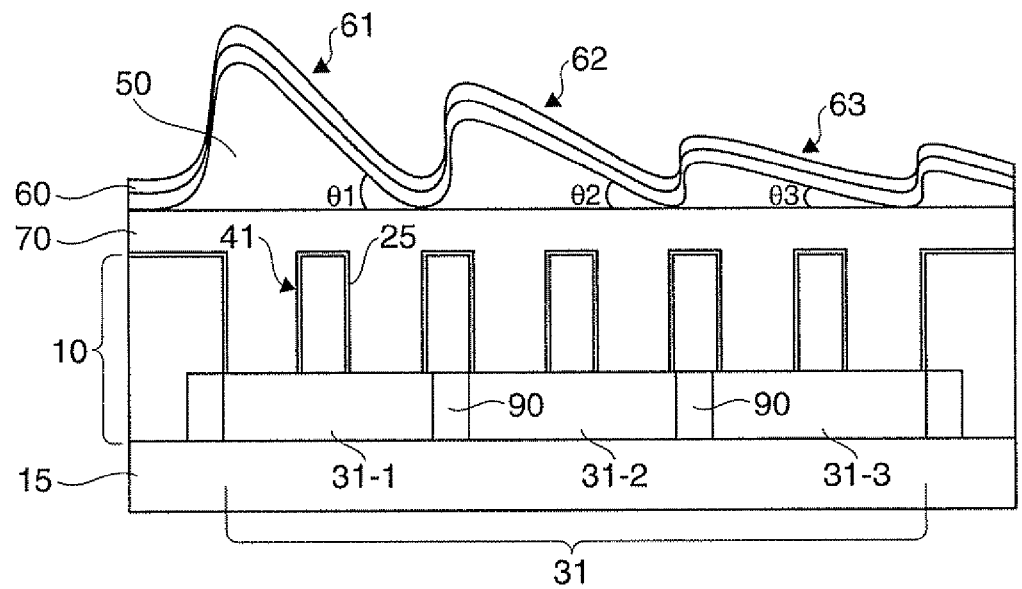
FIG. 5 shows a third modified example of the spectroscopic sensor.

FIG. 5 shows a third modified example of the spectroscopic sensor in which impurity regions for photodiodes are sectioned by trenches. The spectroscopic sensor shown in FIG. 5 includes a semiconductor substrate 10, a wiring layer 15, light blocking materials 25, photodiodes 31, 32, angle limiting filters 41, 42, a tilted structure 50, light band-pass filters 61 to 63, and an insulating layer 70. The photodiode 32, and the light limiting filter 42 are the same as the photodiode 31, and the light limiting filter 41 and their illustration and explanation will be omitted.

In the third modified example, the impurity region of the photodiode 31 is sectioned by trenches 90, and photodiodes 31-1 to 31-3 are formed. The trenches 90 are formed by an insulator trench structure of STI (Shallow Trench Isolation) or the like, for example. On the tilted structure 50, tilted surfaces at tilt angles $\theta 1$ to $\theta 3$ are formed, and the respective tilted surfaces correspond to the photodiodes 31-1 to 31-3, respectively. Then, the light band-pass filters 61 to 63 having different tilt angles are formed on the respective photodiodes 31-1 to 31-3, respectively.

In FIG. 5, one light band-pass filter is provided on one photodiode (one region) sectioned by the trench structure, however, in the embodiment, one light band-pass filter may be provided on plural photodiodes (plural regions) sectioned by the trench structure.

5. Fourth Modified Example

Figure 6:
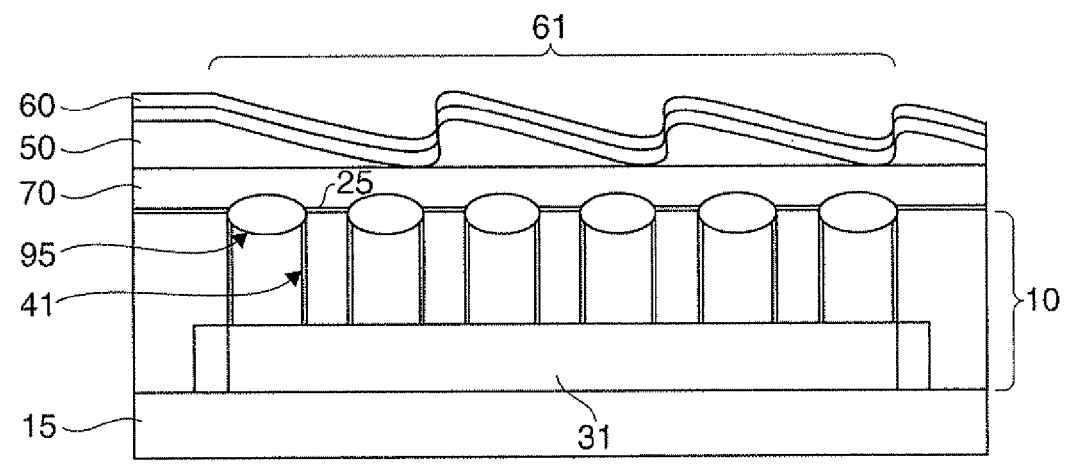
FIG. 6 shows a fourth modified example of the spectroscopic sensor.

FIG. 6 shows a fourth modified example of the spectroscopic sensor in which amounts of incident lights are increased using a micro-lens array (MLA). The spectroscopic sensor shown in FIG. 6 includes a semiconductor substrate 10, a wiring layer 15, light blocking materials 25, photodiodes 31, 32, angle limiting filters 41, 42, a tilted structure 50, light band-pass filters 61, 62, an insulating layer 70, and a micro-lens array 95. The photodiode 32, the angle limiting filter 42, and the light band-pass filter 62 are the same as the photodiode 31, and the angle limiting filter 41, the light band-pass filter 61 and their illustration and explanation will be omitted.

In the fourth modified example, micro-lenses are formed in the respective openings of the angle limiting filter 41, and the micro-lens array 95 is formed by the plural micro-lenses. The micro-lens array collects (focuses in a narrow sense) the incident light to the angle limiting filter 41 on the light receiving surface of the photodiode 31 and increases the light amount of the light receiving surface. For example, the micro-lens array 95 is formed by filling the openings with $SiO_2$ films after formation of the angle limiting filter 41, forming a pattern using photolithography, etching the $SiO_2$ films, and depositing a material with a higher refractive index than that of $SiO_2$, for example.

6. Transmission Wavelength Band of Light Band-Pass Filter

As described above, the transmission wavelength band of the light band-pass filter is set by the tilt angle of the multilayer thin film and the limited angle of the angle limiting filter. This point will specifically be explained using FIGS. 7A and 7B. Note that, for simplicity of explanation, the case where the film thicknesses of the light band-pass filters 61, 62 are the same will be explained as an example as below, however, in the embodiment, the film thicknesses of the light band-pass filters 61, 62 may be different in response to the tilt angles $\theta 1$, $\theta 2$. For example, in deposition of thin films, in the case where the thin films are grown in the perpendicular direction relative to the semiconductor substrate, the film thicknesses of the light band-pass filters 61, 62 may be proportional to cos θ1, cos θ2.

Figure 7A:
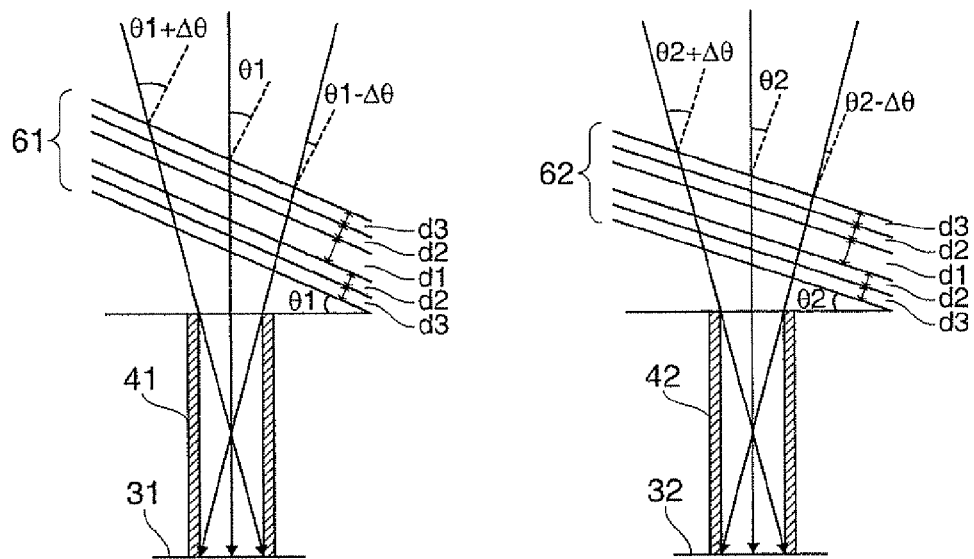
FIGS. 7A and 7B are explanatory diagrams of transmission wavelength bands of light band-pass filters.

As shown in FIG. 7A, the light band-pass filters 61, 62 are formed by thin films having thicknesses d1 to d3 (d2<d1, d3<d1). On and under the thin film having the film thickness d1, plural thin films having thicknesses d2, d3 are alternately stacked. The thin film having the film thickness d2 is formed using a material having different refractive index from those of the thin films having thicknesses d1, d3. Note that, in FIG. 7A, for simplicity, the number of layers of the thin films having thicknesses d2, d3 is omitted, however, in practice, several tens to several hundreds of layers of the thin films are stacked on and under the thin film having the film thickness d1. Further, in FIG. 7A, one layer of the thin film having the film thickness d1 is shown for simplicity, however, in practice, plural layers are often formed.

Since the light band-pass filter 61 has a tilt angle relative to the light receiving surface of the photodiode 31, the beam perpendicular to the light receiving surface enters the light band-pass filter 61 at the angle of θ1. Further, given that the limited angle of the angle limiting filter 41 is Δθ, beams entering the light band-pass filter 61 at (θ1−Δθ) to (θ1+Δθ) reach the light receiving surface of the photodiode 31. Similarly, beams entering the light band-pass filter 62 at (θ2−Δθ) to (θ2+Δθ) reach the light receiving surface of the photodiode 32.

Figure 7B:
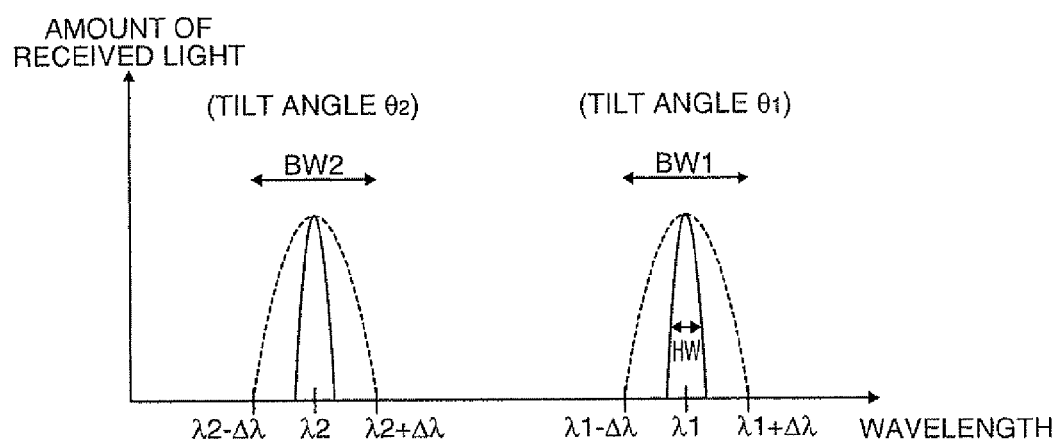

As shown in FIG. 7B, the transmission wavelength band BW1 of the light band-pass filter 61 is (λ1−Δλ) to (λ1+Δλ). In this regard, the transmission wavelength λ1=(2×n×d1×cos θ1) for the beam at the incident angle θ1. Here, n is a refractive index of the thin film having the thickness of d1. Further, (λ1−Δλ)=(2×n×d1×cos(θ1+Δθ)) and (λ1+Δλ)=(2×n×d1×cos(θ1−Δθ)). The half-value width HW (for example, HW<BW1) of the transmission wavelength for the beam at the incident angle θ1 is determined by the number of stacked layers of the multilayer films. The amount of received light of the photodiode 31 is the maximum at the incident angle θ1 perpendicular to the light receiving surface (θ1 with respect to the thin film) and becomes zero at the limited angle, and thus, the amount of received light of the incident light as a whole is represented by a curve shown by a dotted line. The transmission wavelength band BW2 of the light band-pass filter 62 is similarly (λ2−Δλ) to (λ2+Δλ). For example, in the case where θ2<θ1, λ2=(2×n×d1×cos θ2)<λ1=(2×n×d1×cos θ1).

According to the embodiment, the angle limiting filters 41, 42 limit the incident angles of the incident lights to (θ1−Δθ) to (θ1+Δθ), (θ2−Δθ) to (θ2+Δθ) and limit the change ranges of the transmission wavelengths to (λ1−Δλ) to (λ1+Δλ), (λ2−Δλ) to (λ2+Δλ). For the light band-pass filters, the bands BW1, BW2 of the specific wavelengths to be transmitted are set according to the change ranges of the transmission wavelengths limited to (λ1−Δλ) to (λ1+Δλ), (λ2−Δλ) to (λ2+Δλ) by the angle limiting filters 41, 42.

In this manner, the transmission wavelength bands BW1, BW2 of the light band-pass filters may be limited by the angle limiting filters 41, 42, and only the lights in the wavelength bands to be measured may be sensed. For example, the limited angles of the angle limiting filters 41, 42 are set to Δθ≤30°. Desirably, the limited angles of the angle limiting filters 41, 42 are set to Δθ≤20°.

7. Manufacturing Method

An example of a manufacturing method of the spectroscopic sensor of the embodiment in the case where the tilted structure is formed using the semiconductor process will be explained using FIGS. 8 to 14.

Figure 8:
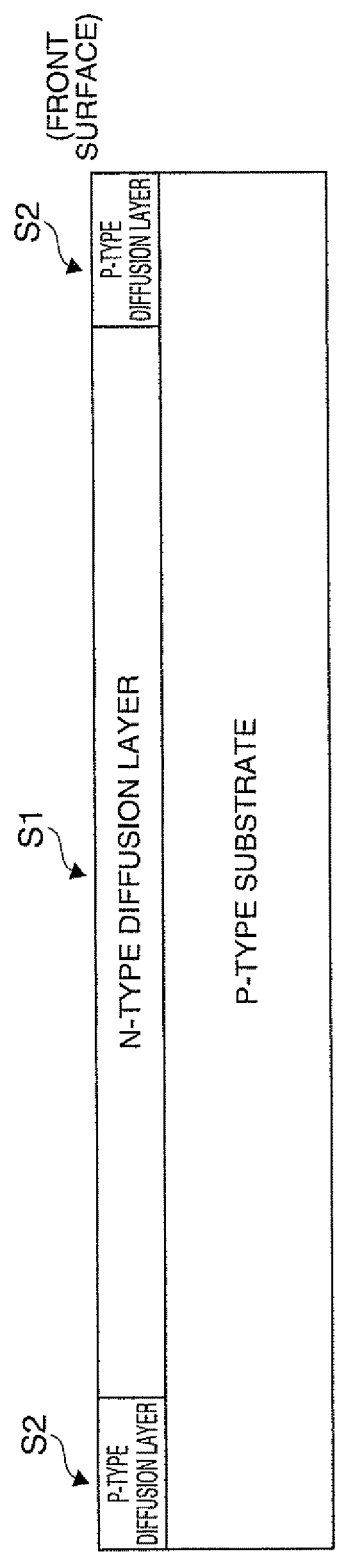
FIG. 8 shows a manufacturing method of the spectroscopic sensor.

First, as shown by S1 in FIG. 8, an N-type diffusion layer (an impurity region of a photodiode) is formed on a P-type substrate at steps of photolithography, ion implantation, and photoresist stripping. As shown by 92, a P-type diffusion layer is formed on the P-type silicon substrate at steps of photolithography, ion implantation, photoresist stripping and thermal treatment. The N-type diffusion layer serves as a cathode of the photodiode, and the P-type diffusion layer (P-type silicon substrate) serves as an anode.

Figure 9:
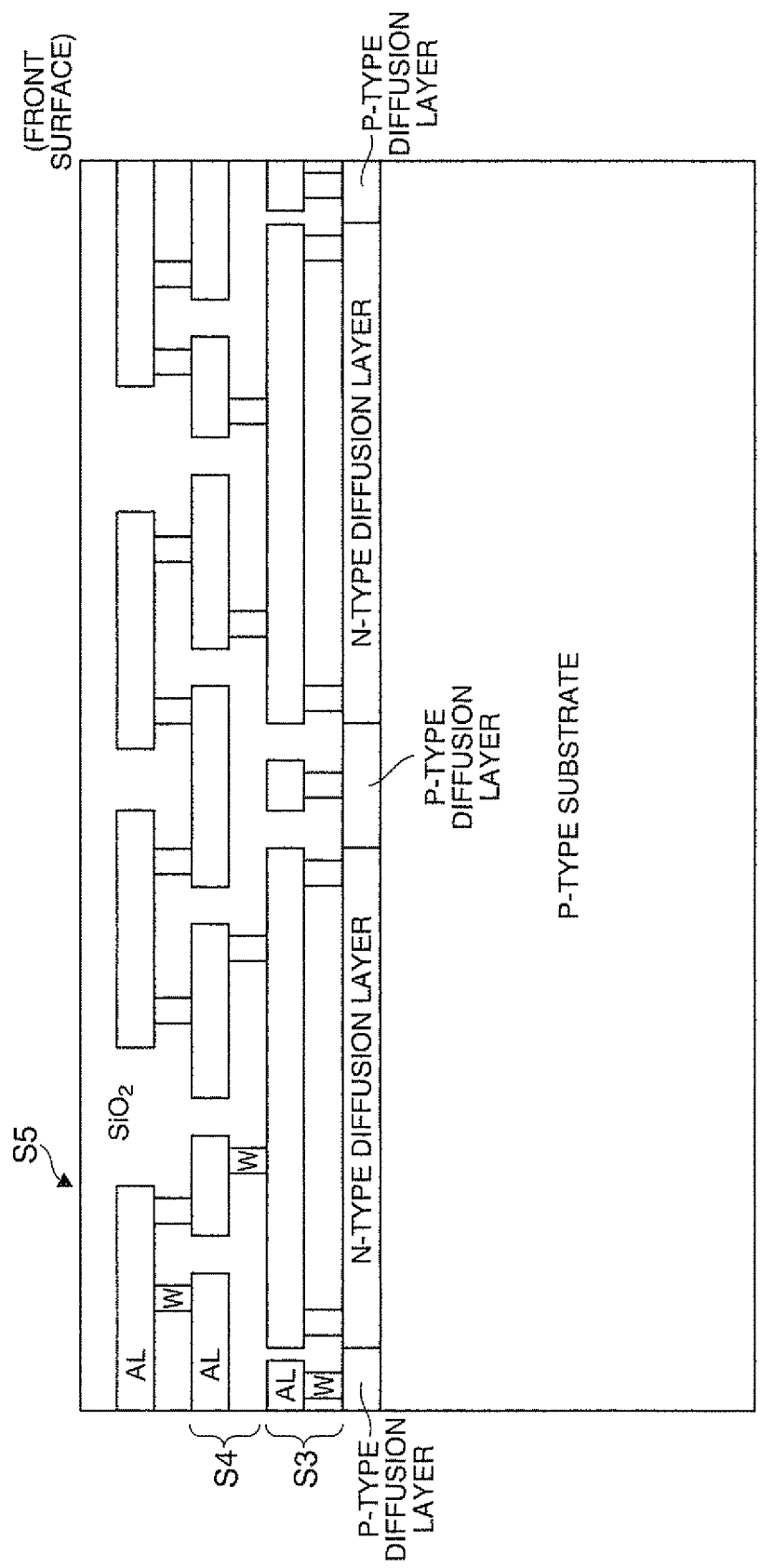
FIG. 9 shows the manufacturing method of the spectroscopic sensor.

Then, as shown by S3 in FIG. 9, at steps of deposition of SiO$_2$, planarization by CMP, an insulating film is formed, and, at steps of photolithography, anisotropic dry etching of SiO$_2$, and photoresist stripping, contact holes are formed. Then, at steps of sputtering of TiN, deposition of W (tungsten), and etching back of W, embedding of contact holes is performed. Then, at steps of sputtering of AL (alum u), sputtering of TiN, photolithography, anisotropic dry etching of AL and TiN, and photoresist stripping, a first AL wiring is formed. The illustration of the TiN film of the contact holes is omitted for simplicity.

Then, as shown by S4, at the same step of S3, via contacts and a second AL wiring are formed, and the same step is repeated at a necessary number of tines and a wiring layer is stacked. FIG. 9 shows the case where the third AL wiring has been formed. As shown by S5, at steps of deposition of SiO$_2$, and planarization by CMP, an insulating film is formed. At steps of polyimide application, and curing, a passivation layer is formed on the insulating layer. In this manner, the wiring layer at the semiconductor substrate front side is formed.

Figure 10:
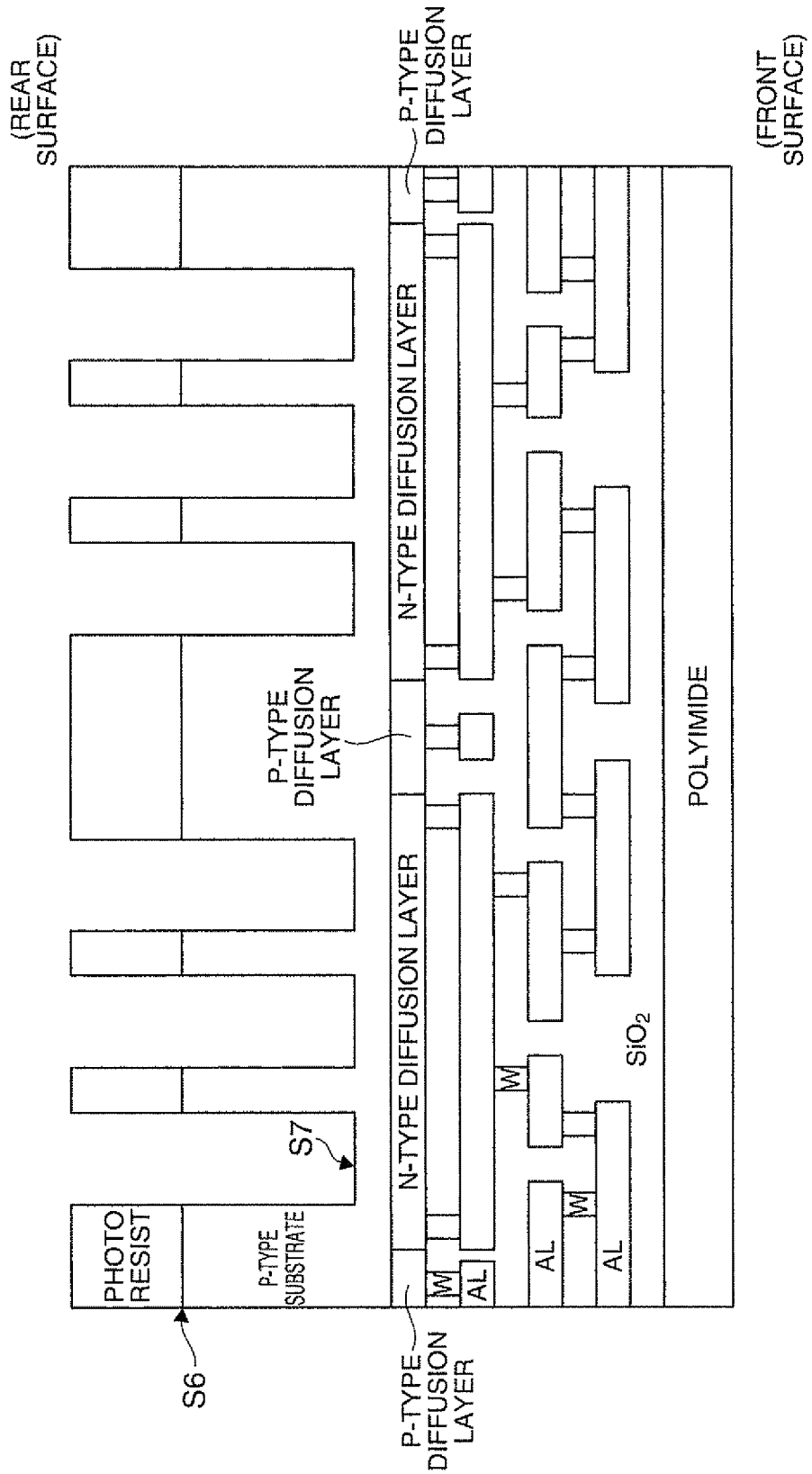
FIG. 10 shows the manufacturing method of the spectroscopic sensor.

Then, as shown by S6 in FIG. 10, the thickness of the P-type silicon substrate is adjusted by grinding the rear surface of the P-type silicon substrate. Then, as shown by S7, at steps of photolithography, anisotropic dry etching of the P-type silicon substrate, and photoresist stripping, silicon trenches are formed.

Figure 11:
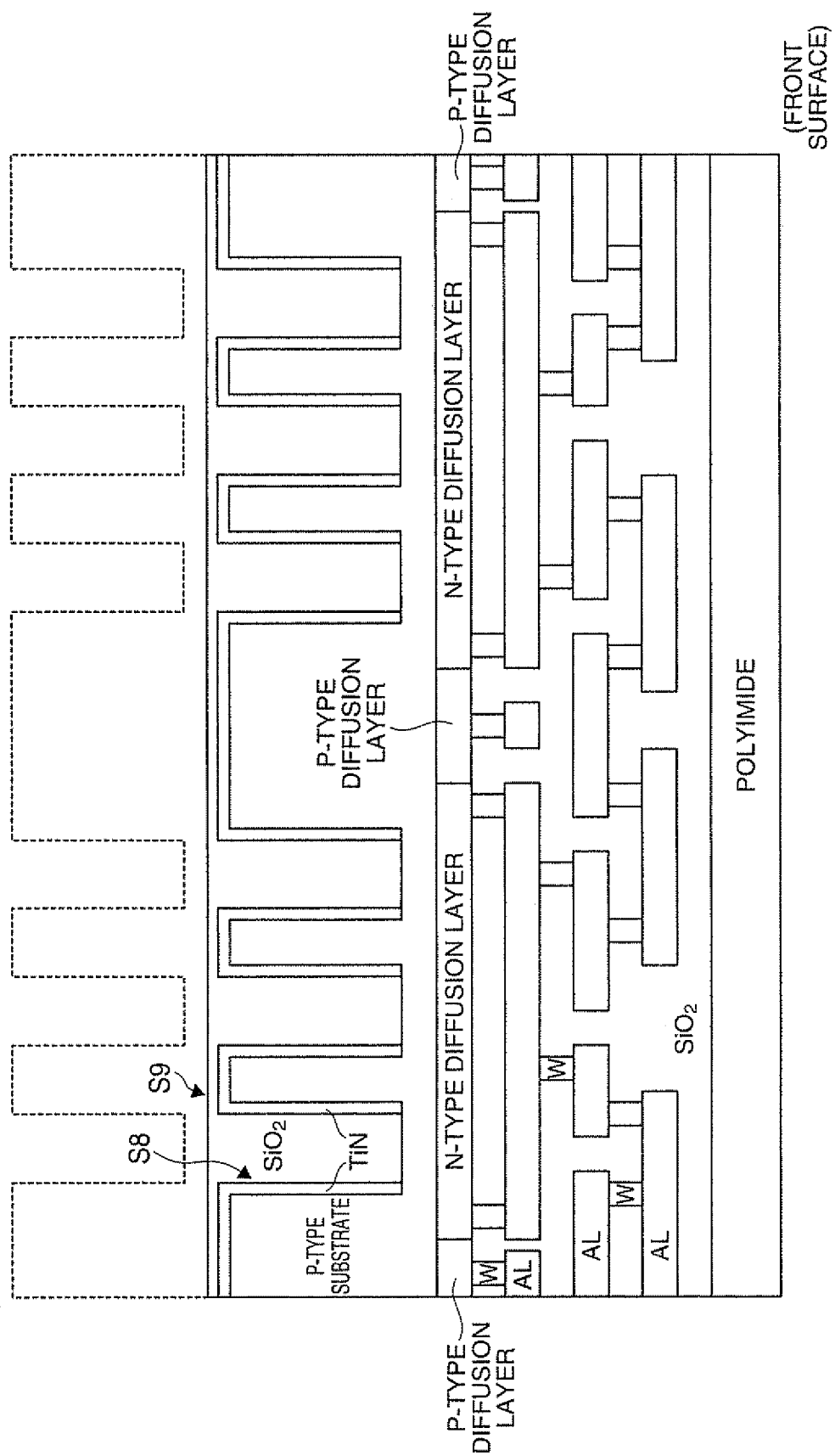
FIG. 11 shows the manufacturing method of the spectroscopic sensor.

Then, as shown by S8 in FIG. 11, at steps of deposition of TiN films, and anisotropic dry etching of the TiN films, light absorbing films (anti-reflection films) of TiN are formed on the side surfaces (inner walls) of the silicon trenches and the rear surface of the semiconductor substrate. Then, as shown by S9, at steps of deposition of an SiO$_2$ film (shown by a dotted line), and planarization of the SiO$_2$ film by CMP, embedding of the silicon trenches are performed. In this manner, the angle limiting filters are formed at the steps of S6 to S9.

Figure 12:
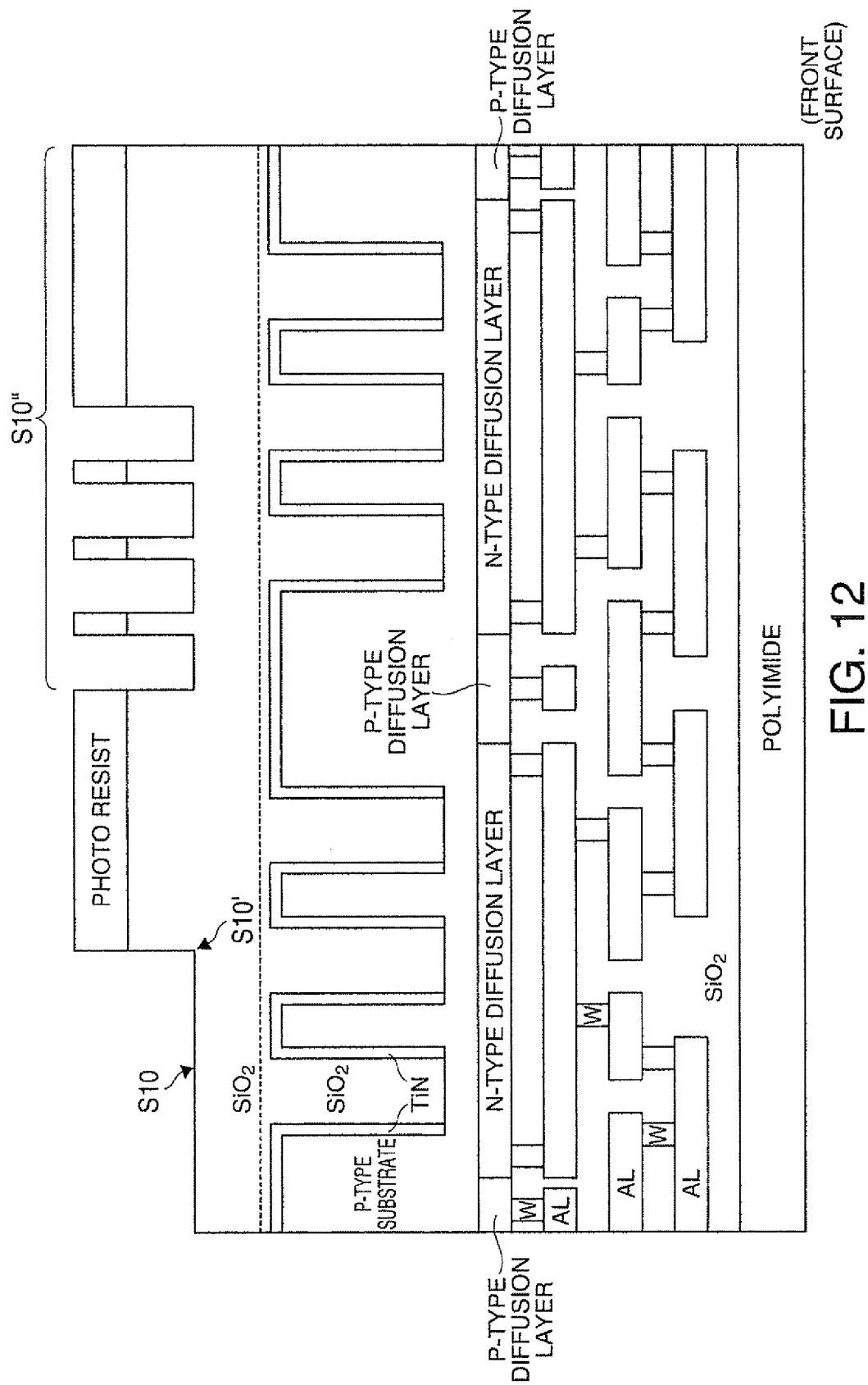
FIG. 12 shows the manufacturing method of the spectroscopic sensor.

Then, as shown by S10 in FIG. 12, at steps of deposition of an SiO$_2$ film, photolithography, anisotropic dry etching of the SiO$_2$ film, and photoresist stripping, steps (S10') or a sparse and dense pattern (S10") of the insulating film is formed.

Figure 13:
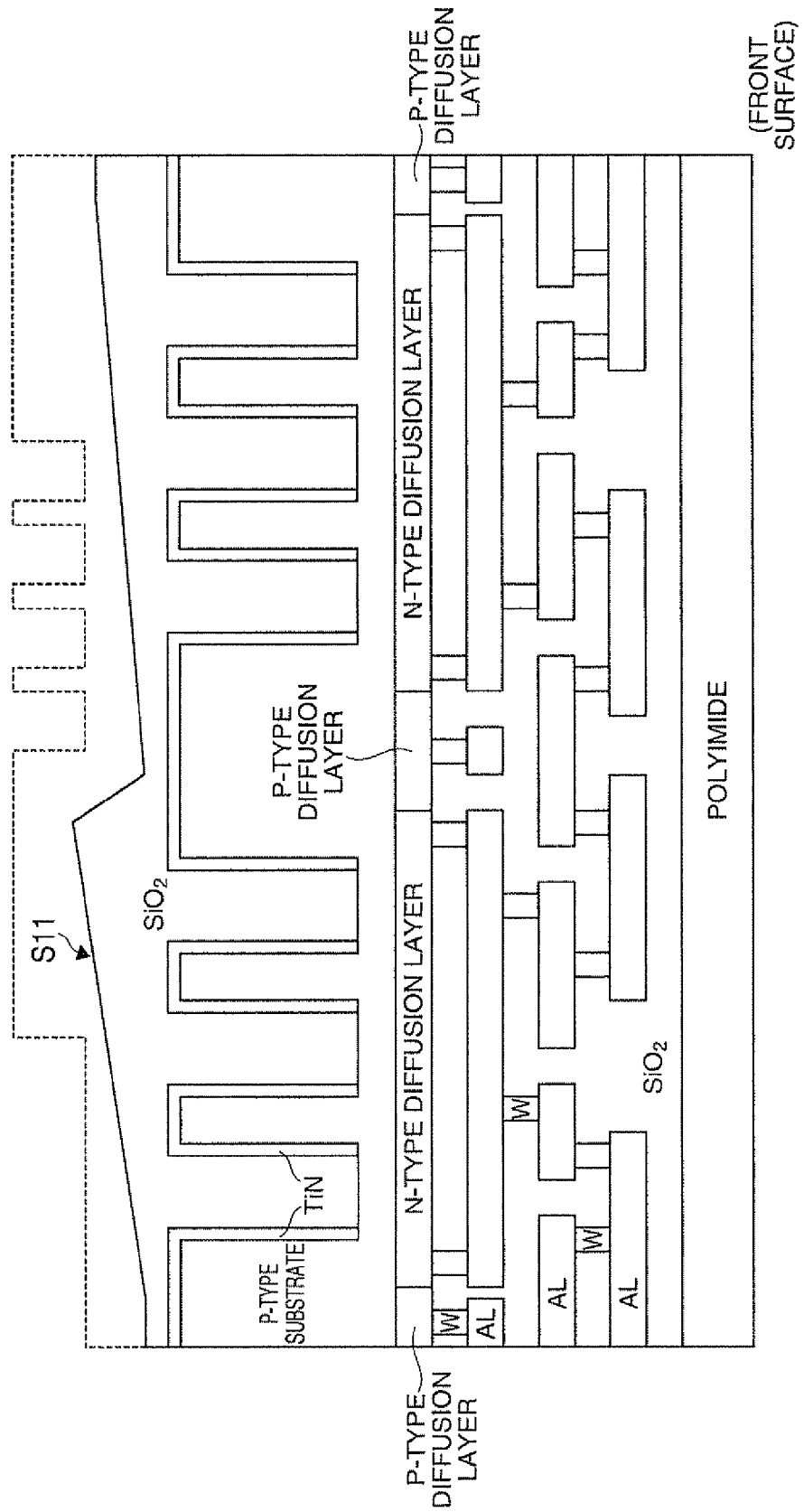
FIG. 13 shows the manufacturing method of the spectroscopic sensor.

Then, as shown by S11 in FIG. 13, at the step of grinding by CMP, tilted surfaces of the tiled structure are formed. The tilted surfaces of the tiled structure are processed at tilt angles in response to the steps or the sparse and dense pattern of the insulating film.

Figure 14:
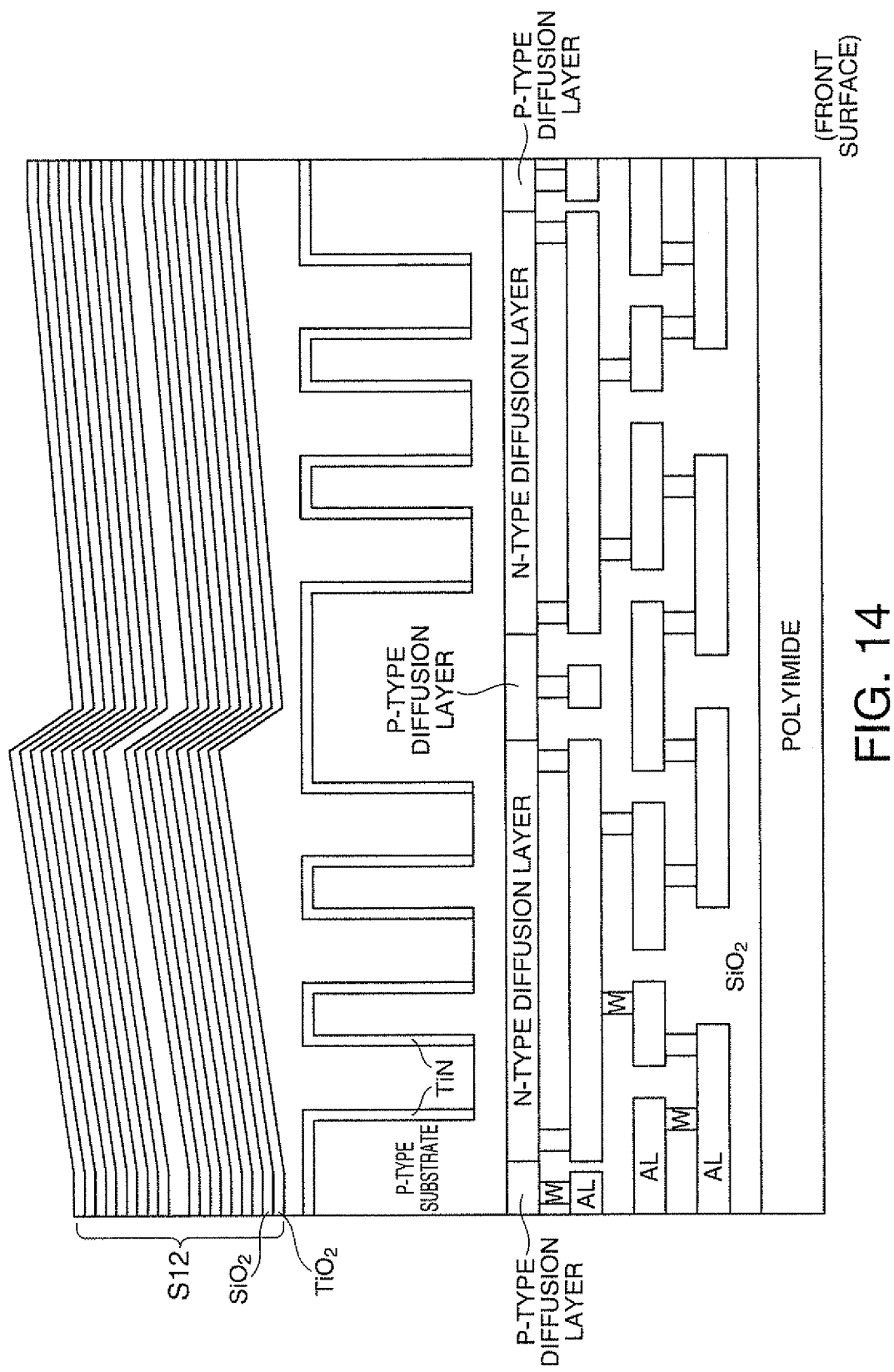
FIG. 14 shows the manufacturing method of the spectroscopic sensor.

Then, as shown by S12 in FIG. 14, a multilayer thin film is formed by alternately performing sputtering of TiO$_2$ (titanium oxide film) and sputtering of SiO$_2$. The TiO$_2$ film is a thin film with a high refractive index, and the SiO$_2$ film is a thin film with a lower refractive index.

8. Manufacturing Method of First Modified Example

An example of a manufacturing method of the spectroscopic sensor of the first modified example of forming the tilted structure using a separate member will be explained using FIGS. 15 to 17.

Figure 15:
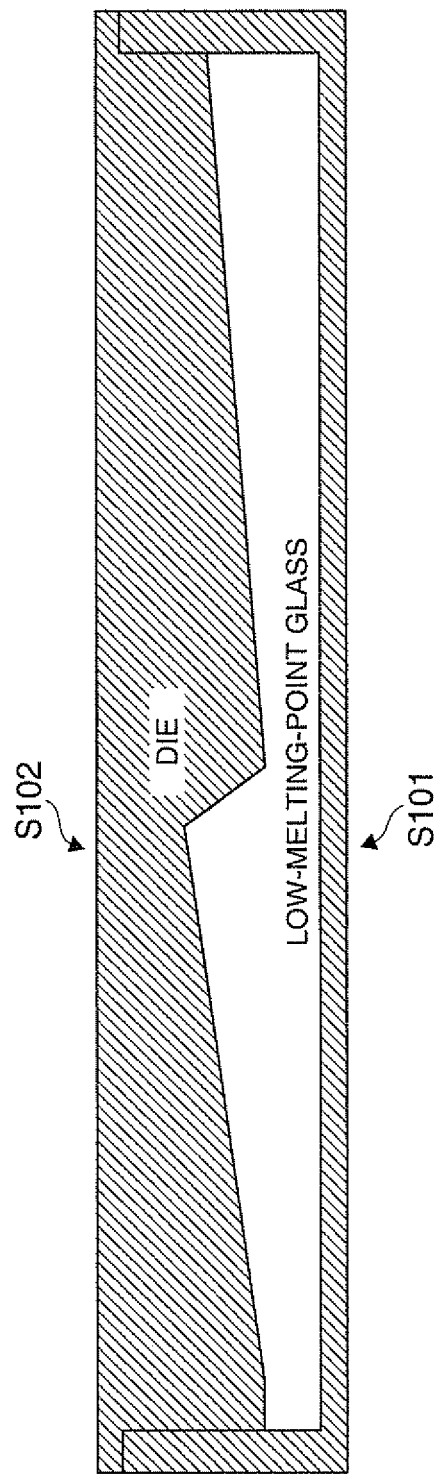
FIG. 15 shows a manufacturing method of a spectroscopic sensor of the first modified example.

First, as shown by S101 in FIG. 15, heated and melted low-melting-temperature glass is poured into a die and, as shown by S102, the low-melting-temperature glass is press-molded using a die with tilted surfaces, and thereby, the tilted structure is formed.

Figure 16:
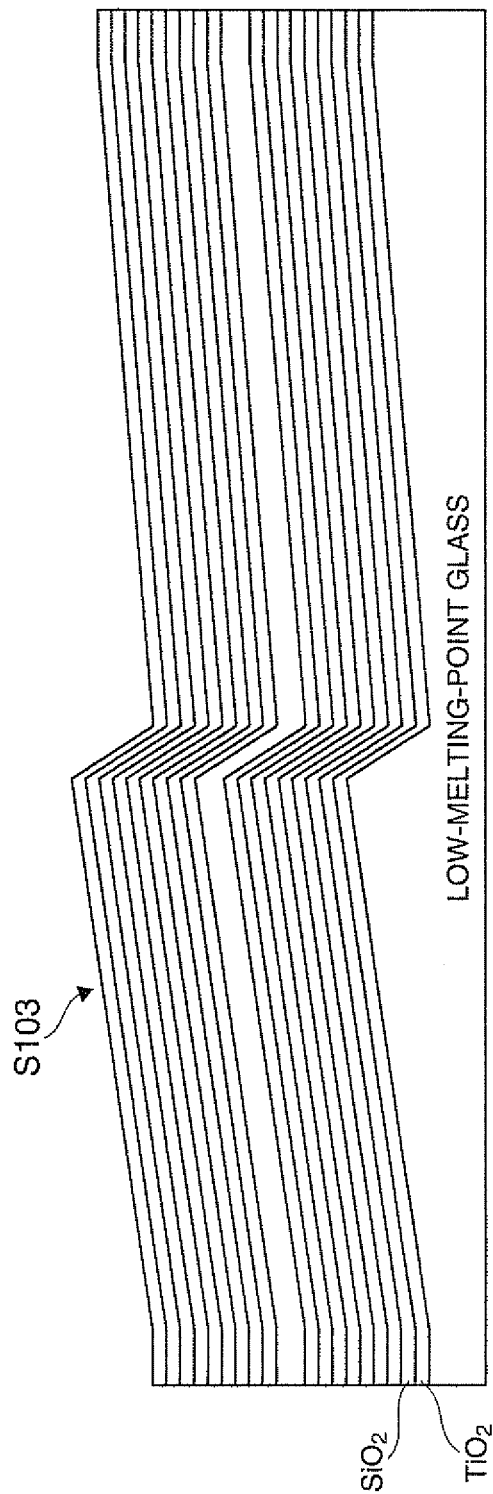
FIG. 16 shows the manufacturing method of the spectroscopic sensor of the first modified example.

Then, as shown by S103 in FIG. 16, by alternating sputtering of $TiO_2$ and sputtering of $SiO_2$, the multilayer thin films are formed on the tilted structure of low-melting-temperature glass.

Figure 17:
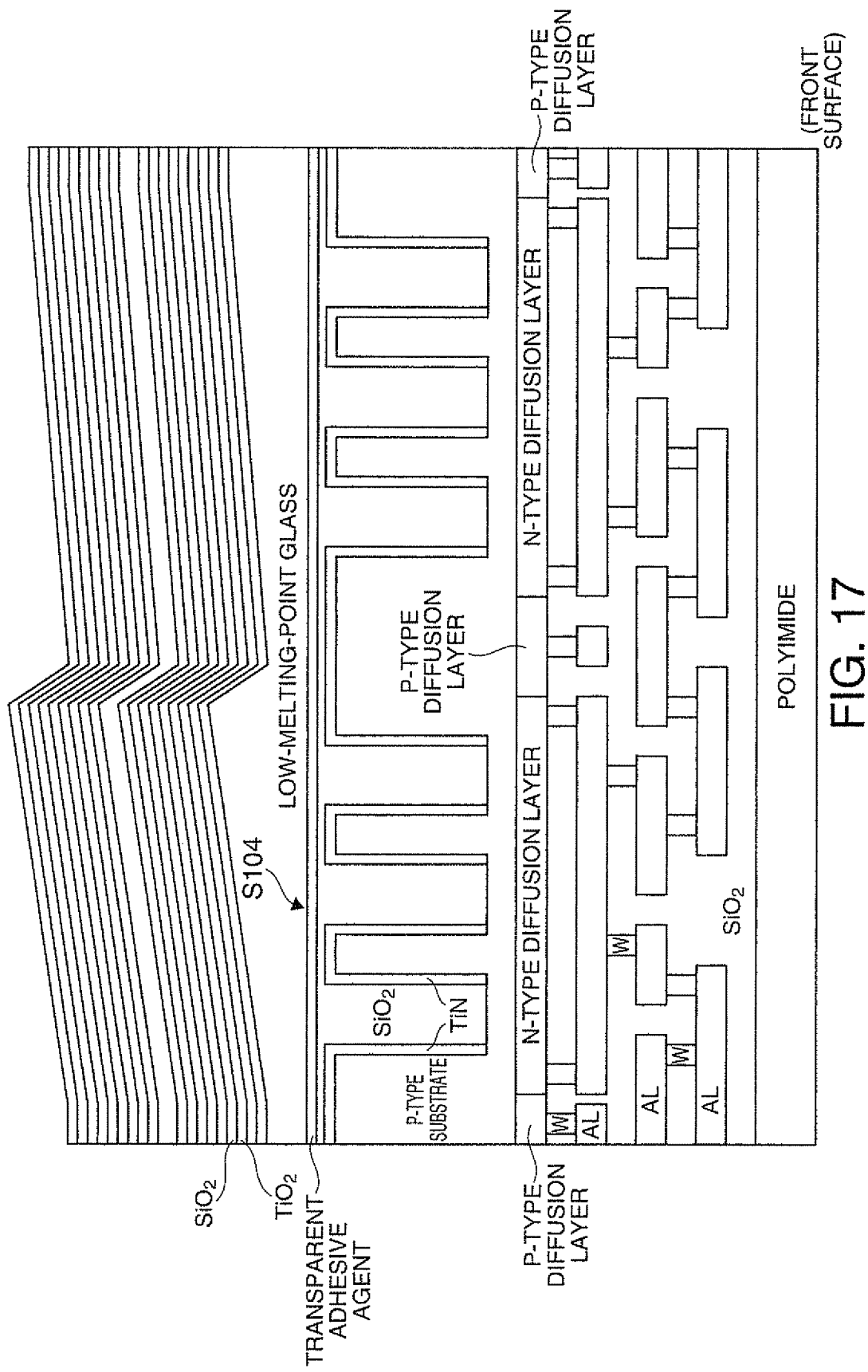
FIG. 17 shows the manufacturing method of the spectroscopic sensor of the first modified example.

Then, as shown by S104 in FIG. 17, the tilted structure on which the multilayer thin films have been formed is bonded to the insulating layer of the angle limiting filters with an adhesive agent (a transparent adhesive agent for the wavelengths to be spectroscopically separated). The photodiodes, the angle limiting filters, and the wiring layer are formed at the steps of S1 to S9 described above in FIGS. 8 to 11.

9. Electronic Apparatus

Figure 18:
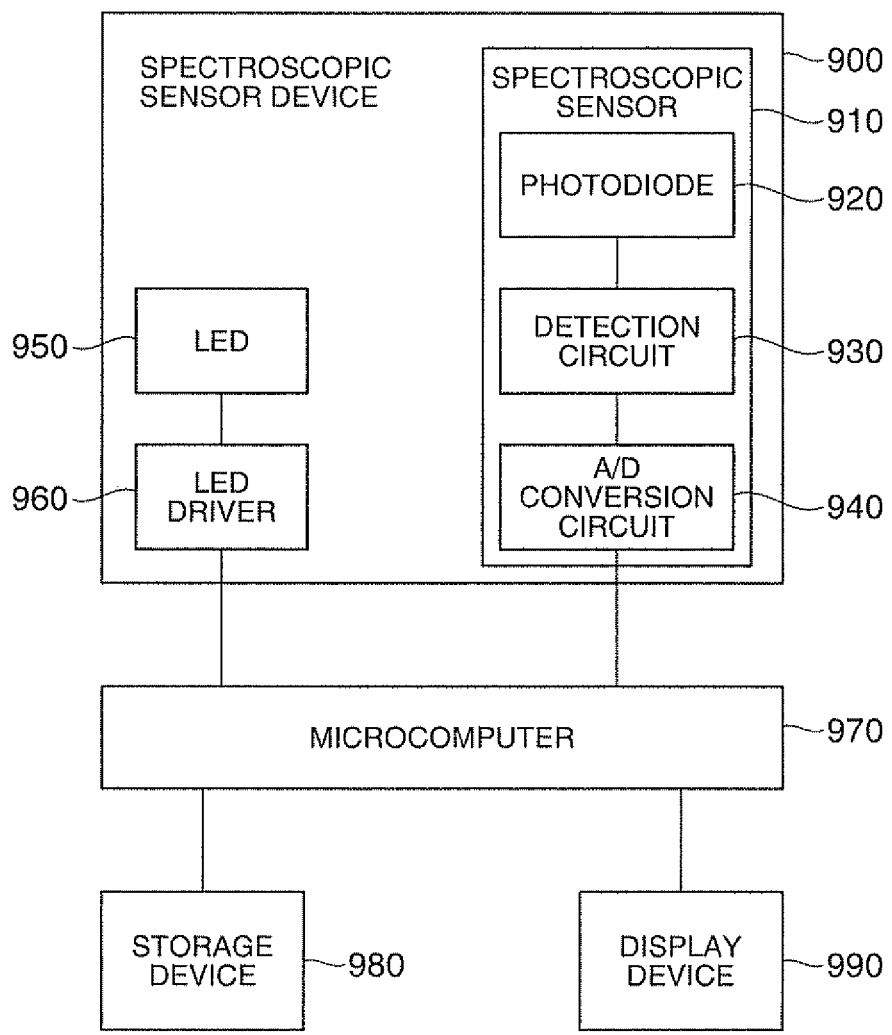
FIG. 18 shows a configuration example of an electronic apparatus.

FIG. 18 shows a configuration example of an electronic apparatus including the spectroscopic sensor of the embodiment. For example, as an electronic apparatus, a pulsimeter, a pulse oximeter, a blood sugar meter, a fruit sugar content meter, or the like is assumed.

The electronic apparatus shown in FIG. 18 includes a spectroscopic sensor device 900, a microcomputer 970 (CPU), a storage device 980, and a display device 990. The spectroscopic sensor device 900 includes an LED 950 (light source), an LED driver 960, and a spectroscopic sensor 910. The spectroscopic sensor 910 is integrated in one chip of IC, for example, and includes a photodiode 920, a detection circuit 930, and an A/D conversion circuit 940.

The LED 950 applies white light, for example, to an object of observation. The spectroscopic sensor device 900 spectroscopically separates the reflected light and the transmitted light from the object of observation, and acquires signals of the respective wavelengths. The microcomputer 970 controls the LED driver 960 and acquires signals from the spectroscopic sensor 910. The microcomputer 970 displays representation based on the acquired signals on the display device 990 (for example, a liquid crystal display device) or stores data based on the acquired signals in the storage device 980 (for example, a memory or a magnetic disc).

The embodiment has been specifically explained as described above, however, a person skilled in the art may easily understand that many modifications without substantially departing from new matter and effects of the invention may be made. Therefore, the modified examples are within the scope of the invention. For example, in specifications or drawings, terms (photodiode, light band-pass filter, silicon substrate, etc.) described with terms (photosensor, thin-film filter, semiconductor substrate, etc.) in broader senses or synonyms at least at once may be replaced by the different terms in any part of the specifications or drawings. Further, the configurations and operations of the spectroscopic sensor, the spectroscopic sensor device, an electronic apparatus, etc. are not limited to those that have been explained in the embodiment, but various changes may be embodied.

What is claimed is:

1. A spectroscopic sensor comprising:
    an impurity region for a photodiode formed in a semiconductor substrate; and
    an angle limiting filter for limiting an incident angle of an incident light to a light receiving surface of the photodiode, the angle limiting filter formed directly above the impurity region,
    wherein, the angle limiting filter comprises a substantially vertically extended substrate portion of said semiconductor substrate disposed along a circumference of a surface of the impurity region, and a light blocking material is directly provided on side surfaces of the substantially vertically extended substrate portion.

2. The spectroscopic sensor according to claim 1, further comprising
    a light band-pass filter that transmits a specific wavelength of the incident light, the light band-pass filter formed over the angle limiting filter.

3. The spectroscopic sensor according to claim 2, wherein the light band-pass filter has a transmission wavelength that varies in response to the incident angle of the incident light to the light receiving surface of the photodiode,
    the angle limiting filter limits the incident angle of the incident light and limits a change range of the transmission wavelength, and
    for the light band-pass filter, a band of the specific wavelength to be transmitted is set according to the change range of the transmission wavelength limited by the angle limiting filter.

4. The spectroscopic sensor according to claim 1, wherein the angle limiting filter is formed along an outer circumference of a light receiving area of the photodiode in a plan view with respect to the semiconductor substrate.

5. The spectroscopic sensor according to claim 1, wherein the angle limiting filter has plural openings formed on a rear surface side of the semiconductor substrate, and
    the plural openings are formed along an outer circumference of the light receiving area of the photodiode and limits the incident angle of the incident light to the light receiving area of the photodiode.

6. The spectroscopic sensor according to claim 2, wherein the light band-pass filter is formed by a multilayer thin film tilted at an angle in response to the transmission wavelength relative to the semiconductor substrate.

7. The spectroscopic sensor according to claim 6, wherein the light band-pass filter is formed by plural sets of multilayer thin films having different transmission wavelengths, and
    the plural sets of multilayer thin films have different tilt angles relative to the semiconductor substrate in response to the transmission wavelengths and are formed in a simultaneous thin film forming step.

8. The spectroscopic sensor according to claim 6, wherein the impurity region for the photodiode is sectioned into plural regions by an insulator having a trench structure,
    the light band-pass filter is formed by plural band-pass filters having different transmission wavelengths, and
    each band-pass filter of the plural light band-pass filters is provided in response to one or some regions sectioned by the insulator having the trench structure.

9. The spectroscopic sensor according to claim 6, further comprising
    a tilted structure provided on the angle limiting filter,
    wherein the tilted structure has a tilted surface tilted at an angle in response to the transmission wavelength of the light band-pass filter relative to the semiconductor substrate, and
    the multilayer thin film is formed on the tilted surface.

10. The spectroscopic sensor according to claim 9, wherein the tilted structure is formed on the angle limiting filter using a semiconductor process.

11. The spectroscopic sensor according to claim 10, wherein, the tilted structure is formed by forming a step or a sparse and dense pattern on a transparent film stacked by the semiconductor process, and performing at least one of grinding and etching on the step or the sparse and dense pattern.

12. The spectroscopic sensor according to claim 1, wherein the light blocking material is further provided on the rear surface of the extended substrate portion.

13. The spectroscopic sensor according to claim 12, wherein
the light blocking material is a light absorbing material or a light reflecting material.

14. An electronic apparatus comprising the spectroscopic sensor according to claim 1.

15. An electronic apparatus comprising the spectroscopic sensor according to claim 3.

16. An electronic apparatus comprising the spectroscopic sensor according to claim 4.

17. An electronic apparatus comprising the spectroscopic sensor according to claim 5.

18. An electronic apparatus comprising the spectroscopic sensor according to claim 6.

19. An electronic apparatus comprising the spectroscopic sensor according to claim 9.

20. An electronic apparatus comprising the spectroscopic sensor according to claim 10.

21. An electronic apparatus comprising the spectroscopic sensor according to claim 12.

* * * * *